(12) United States Patent
Takalo et al.

(10) Patent No.: US 8,216,856 B2
(45) Date of Patent: Jul. 10, 2012

(54) LUMINESCENT LANTHANIDE LABELLING REAGENTS AND THEIR USE

(75) Inventors: Harri Takalo, Turku (FI); Jouko Kankare, Turku (FI); Elina Tienari, Espoo (FI)

(73) Assignee: Abacus Diagnostica Oy, Turku (FI)

( * ) Notice: Subject to any disclaimer, the term of this patent is extended or adjusted under 35 U.S.C. 154(b) by 330 days.

(21) Appl. No.: 12/310,202

(22) PCT Filed: Aug. 17, 2007

(86) PCT No.: PCT/FI2007/000202
§ 371 (c)(1), (2), (4) Date: Aug. 3, 2009

(87) PCT Pub. No.: WO2008/020113
PCT Pub. Date: Feb. 21, 2008

(65) Prior Publication Data
US 2010/0081211 A1 Apr. 1, 2010

Related U.S. Application Data

(60) Provisional application No. 60/838,430, filed on Aug. 18, 2006.

(30) Foreign Application Priority Data

Aug. 18, 2006 (FI) ..................................... 20060735

(51) Int. Cl.
*G01N 33/532* (2006.01)
*G01N 33/24* (2006.01)
*G01N 21/76* (2006.01)
*G01N 33/53* (2006.01)

(52) U.S. Cl. ............. 436/546; 436/81; 436/172; 435/7.1

(58) Field of Classification Search ........................ None
See application file for complete search history.

(56) References Cited

U.S. PATENT DOCUMENTS

| 4,761,481 A | 8/1988 | Hale et al. |
| 5,055,578 A | 10/1991 | Hale et al. |
| 5,252,720 A | 10/1993 | Sessler et al. |
| 7,018,851 B2 | 3/2006 | Takalo et al. |
| 2005/0181393 A1 | 8/2005 | Hovinen et al. |

FOREIGN PATENT DOCUMENTS

| WO | WO 2005/021538 A1 | 3/2005 |
| WO | WO 2005/058877 A1 | 6/2005 |

OTHER PUBLICATIONS

Bush, C. E. et al., "Solid-Phase Time-Resolved Fluorescence Detection of Human Immunodeficiency Virus Polymerase Chain Reaction Amplification Products," *Anal. Biochem.* 1992, 202, p. 146-151.
Hemmilä, I. et al., "Di- and tetracarboxylate derivatives of pyridines, bipyridines and terpyridines as luminogenic reagents for time-resolved fluorometric deteimination of terbium and dysprosium," *J. Biochem. Biophys. Methods* 1993, 26, p. 283-290.
Latva, M. et al., "Correlation between the lowest triplet state energy level of the ligand and lanthanide(III) luminescence quantum yield," *J. Luminescence* 1997, 75, p. 149-169.
Sato, N. et al., "Energy-transfer Luminescence of Lanthanide Ions Encapsulated in Sensitizer-modified Calix[4]arenes," *J. Chem. Soc. Perkin Trans.* 1993, 2, p. 621-624.
Steemers, F. J. et al., "New Sensitizer-Modified Calix[4]arenes Enabling Near-UV Excitation of Complexed Luminescent Lanthanide Ions," *J. Am. Chem. Soc.* 1995, 117, p. 9408-9414.
Selvin, P. R. et al., "Luminescence Resonance Energy Transfer," *J. Am. Chem. Soc.* 1994, 116, p. 6029-6030.
Jaakkola, L. et al., "Solid-Phase Synthesis of Oligonucleotides Labeled with Luminescent Lanthanide(III) Chelates," *Bioconjugate Chem.* 2005, 16, p. 700-709. Sabbatini, N. et al., "Lanthanide luminescence in supramolecular species," *J. Luminescence* 1991, 48 & 49, p. 463-468.
Hemmilä, I. et al., "Development of luminescent lanthanide chelate labels for diagnostic assays," *J. of Alloys and Compounds* 1997, 249, p. 158-162.
International Search Report in PCT/FI2007/000202, dated Feb. 6, 2008.
Search Report issued by National Board of Patents and Registration of Finland in Patent No. 20060735, dated Jun. 18, 2007.

(Continued)

*Primary Examiner* — Shafiqul Haq
(74) *Attorney, Agent, or Firm* — Buchanan Ingersoll & Rooney PC

(57) ABSTRACT

The invention relates to a detectable molecule comprising a biospecific binding reactant attached to a luminescent lanthanide chelate comprising a lanthanide ion and a chelating ligand of the formula (I)

(I)

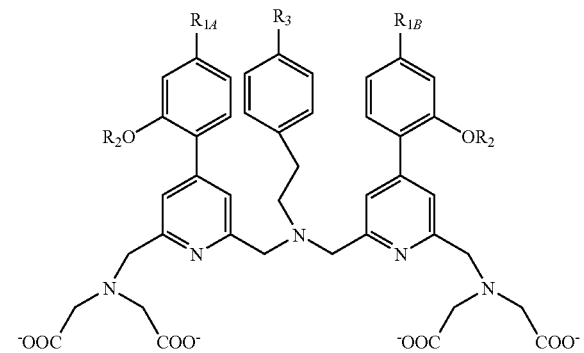

wherein, $R_{1A}$ $R_{1B}$ are independently of each other selected from the group consisting of hydrogen, methyl, ethyl, —COOH, —COO—, —CH$_2$COOH, —CH$_2$COO—, hydroxyl or OR$_2$; R$_2$ is selected from the group consisting of —CH$_3$, —C(CH$_3$)$_3$, —C(CR$_4$)$_3$, wherein R$_4$ is an alkyl with 1 to 6 carbon atoms, —CH$_2$COOH, —CH$_2$COO$^-$, and appropriate hexose residues; R$_3$ is a linker for coupling to a biospecific binding reactant selected from the group consisting of thiourea (—NH—CS—NH—), aminoacetamide (—NH—CO—CH$_2$—NH—), amide (—NH—CO— and —CO—NH—), aliphatic thioether (—S—), disulfide (—S—S—) and 6-substituted-1,3,5-triazine-2,4-diamine; and the lanthanide ion is selected from the group consisting of europium (III), terbium(III), dysprosium(III) and samarium(III). The invention also relates to corresponding lanthanide chelates. The invention further relates to the use of the detectable molecule of the invention.

13 Claims, No Drawings

OTHER PUBLICATIONS

PCT Written Opinion of the International Searching Authority in PCT/FI2007/000202, dated Feb. 6, 2008.

Takalo, H., et al., "Synthesis and Luminescence of Novel $EU^{III}$ Complexing Agents and Labels with 4-(Phenylethynyl)pyridine Subunits," *Helvetica Chimica Acta*, 1996, 79, 789-802.

Von Lode, Piia, et al., "A Europium Chelate for Quantitative Point-of-Care Immunoassays Using Direct Surface Measurement," *Anal Chem.* 2003, 75, 3193-3201.

Karsulayan, Huriye, et al., "Influence of Coupling Method on the Luminescence Properties, Coupling Efficiency, and Binding Affinity of Antibodies Labeled with Europium (III) Chelates," *Bioconjugate Chem.*, 1997, 8, 71-75.

LUMINESCENT LANTHANIDE LABELLING REAGENTS AND THEIR USE

FIELD OF THE INVENTION

The present invention relates to detectable lanthanide chelates to be attached to a biospecific binding reactant to form detectable molecules and use of the detectable molecules in bioaffinity based binding assays.

BACKGROUND OF THE INVENTION

The publications and other materials used herein to illuminate the background of the invention, and in particular, cases to provide additional details respecting the practice, are incorporated by reference.

In biospecific binding assays, such as, e.g. immunoassays, nucleic acid hybridization assays, receptor-binding assays, and cellular binding assays, the analytes to be measured are generally present at very low concentrations. Various labelling compounds have been developed that allow labelling reactants to be detected and quantitated at high sensitivity. Time-resolved luminescence spectroscopy using lanthanide chelates has for several years been applied in immunoassays and nucleic acid hybridization assays [e.g. I. Hemmilä, T. Stålberg, and P. Mottram (eds.), "Bioanalytical Applications of Labelling Technologies", Wallac, Turku, 1994 and D. Wild (eds), "The Immunoassay Handbook", Nature Publishing Group, 2001]. Stable photoluminescent (referred in the context of this specification simply as luminescent) lanthanide chelates have also other applications, e.g. fluorescence microscopy and cytometry. Therefore, a number of attempts have been made to develop new highly luminescent chelates suitable for those types of time-resolved fluorometric applications. These include e.g. stable chelates composed of derivatives of pyridine (U.S. Pat. No. 4,920,195; U.S. Pat. No. 4,801,77; U.S. Pat. No. 4,761,481; Bush. C. E. et al. 1992, Anal. Biochem., 202,146; WO 92/14841; Hemmilä, et al., 1993, J. Biochem. Biophys. Methods, 26, 283; U.S. Pat. No. 5,571,897; U.S. Pat. No. 5,859,215, Latva, M. et al., 1997, J. Luminescence, 75, 149; Takalo, H. et al., 1996, Helv. Chim. Acta, 79, 789; von Lode, P. et al., 2003, Anal. Chem. 75, 3193; U.S. Pat. No. 7,018,851; WO 2005/021538; US 2005/0181393); bipyridines (U.S. Pat. No. 5,216,134), terpyridines (U.S. Pat. No. 4,859,777; U.S. Pat. No. 5,202,423; U.S. Pat. No. 5,324,825) or various phenolic compounds (U.S. Pat. No. 4,670,572; U.S. Pat. No. 4,794,191; IT 1235668) as the energy mediating groups and polycarboxylic acids as chelating parts. In addition, various dicarboxylate derivatives (U.S. Pat. No. 5,032,677; U.S. Pat. No. 5,055,578; U.S. Pat. No. 4,772,563), macrocyclic cryptates (U.S. Pat. No. 4,927,923; WO 93/5049; EP 0 493 745), calixarenes (Sato, N. et al., 1993, J. Chem. Soc. Perkin Trans. 2, 621; Steemers, F. J. et al., 1995, J. Am. Chem. Soc., 117, 9408), DTPA carbostril 124 conjugate (Selvin, P. R., et al., 1994, J. Am. Chem. Soc., 116, 6029) and macrocyclic Schiff bases (EP 0 369 000) have been disclosed in patent applications and/or patents.

Since the publication of chelates, which contain two and three separate 4-(phenylethynyl)pyridine moieties (Takalo, H. et al., Helv. Chim. Acta, 79, 789) the designed chelating structures have been applied in patent applications and publications where the phenylethynyl substituents have been replaced with 2-furyls and trialkoxyphenyls (WO 2005/021538; US 2005/0181393, Jaakkola, L. et al. 2005, Bioconjugate Chem., 16, 700). Moreover, by combining two reactive functional groups for coupling the label to a biospecific binding reactant highly luminescent chelates have been obtained (U.S. Pat. No. 7,018,851). Chelates with 2,4,6-trimethoxypyridine chromophores have shown high luminescence especially with Tb(III) and Dy(III) ions (U.S. Pat. No. 4,761,481; Hemmilä, et al, 1993, J. Biochem. Biophys. Methods, 26, 283; Latva, M. et al., 1997, J. Luminescence, 75, 149, US 2005/0181393; Jaakkola, L. et al. 2005, Bioconjugate Chem., 16, 700). The triplet-state energy level of the ligand, the nature of the chromophore and the biomolecule binding group have significant effect on the luminescent properties of the Tb(III) labels (see e.g. Sabbatini, N. et al., 1991, J. Luminescence 48 & 49: 463; Hemmilä, et al., 1997, J. of Alloys and Compounds 249, 158). Thus even small changes in chelate structure may significantly reduce luminescence of Tb(III) labels.

It is known that the addition of chromophores decreases the solubility of ligands and chelates in water, increases the formation of biospecific binding reactant aggregates during the labelling process and non-specific binding properties of labelled biomolecules. Aggregates will produce purification problems and reduced yield of labelled material. Moreover, increased non-specific binding of labelled biomolecule will enhance background luminescence of biospecific assays and thus reduces assay sensitivity.

OBJECTS AND SUMMARY OF THE PRESENT INVENTION

One object of the present invention is to provide a detectable molecule comprising a biospecific binding reactant attached to a luminescent lanthanide chelate.

Another object of the present invention is to provide a luminescent lanthanide chelate.

A further object of the present invention is to provide use of the detectable molecule of the invention in a biospecific binding assay.

Thus, this invention provides a detectable molecule comprising a biospecific binding reactant attached to a luminescent lanthanide chelate comprising a lanthanide ion and a chelating ligand of the formula (I)

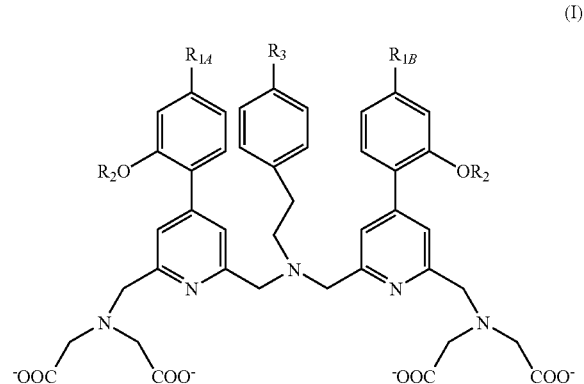

(I)

wherein, a) $R_{1A}$ and $R_{1B}$ are independently of each other selected from the group consisting of hydrogen, methyl, ethyl, —COON, —COO—, —CH$_2$COOH, —CH$_2$COO—, hydroxyl or $OR_2$;

b) $R_2$ is selected from the group consisting of —CH$_3$, —C(CH$_3$)$_3$, —C(CR$_4$)$_3$, wherein $R_4$ is an alkyl with 1 to 6 carbon atoms, —CH$_2$COOH, —CH$_2$COO$^-$,

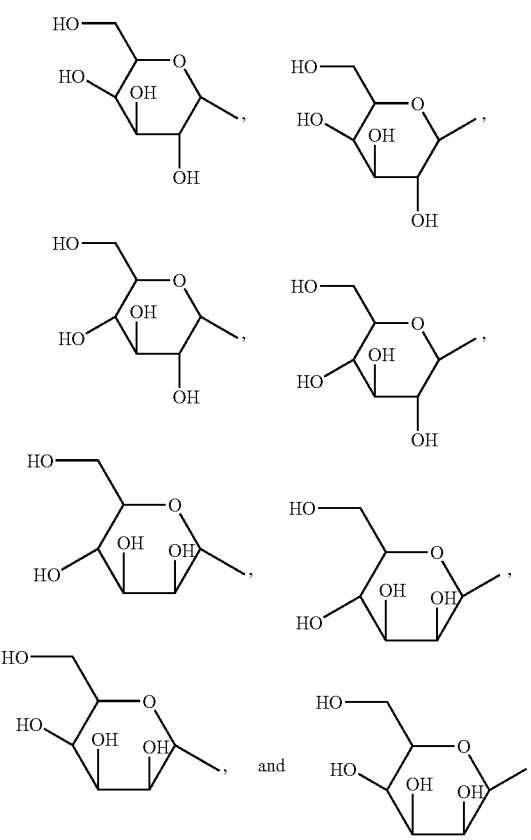

c) $R_3$ is a linker for coupling to a biospecific binding reactant selected from the group consisting of thiourea (—NH—CS—NH—), aminoacetamide (—NH—CO—CH$_2$—NH—), amide (—NH—CO— and —CO—NH—), aliphatic thioether (—S—), disulfide (—S—S—) and 6-substituted-1,3,5-triazine-2,4-diamine; and d) the lanthanide ion is selected from the group consisting of europium(III), terbium(III), dysprosium(III) and samarium (III).

The invention also provides a luminescent lanthanide chelate comprising a lanthanide ion and a chelating ligand of formula (I)

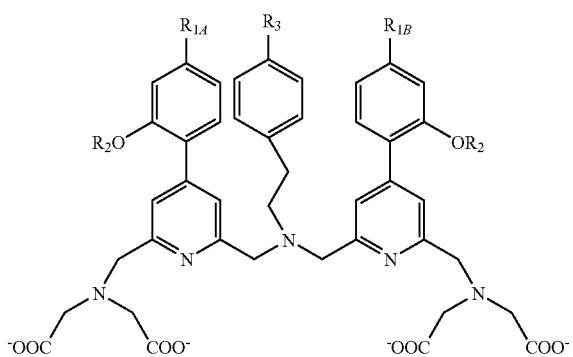

wherein, a) $R_{1A}$ and $R_{1B}$ are independently of each other selected from the group consisting of hydrogen, methyl, ethyl, —COON, —COO—, —CH$_2$COOH, —CH$_2$COO—, hydroxyl or $OR_2$;

b) $R_2$ is selected from the group consisting of —CH$_3$, —C(CH$_3$)$_3$, —C(CR$_4$)$_3$, wherein $R_4$ is an alkyl with 1 to 6 carbon atoms, —CH$_2$COOH, —CH$_2$COO—,

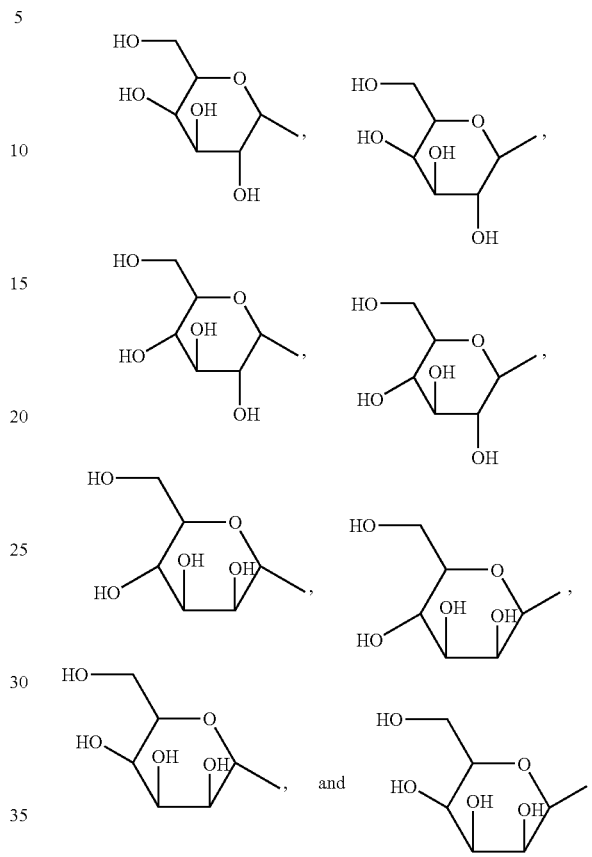

c) $R_3$ is a linker for coupling to a biospecific binding reactant selected from the group consisting of amino, aminooxy, carboxyl, aldehyde or mercapto groups and activated derivatives thereof; and d) the lanthanide ion is selected from the group consisting of europium(III), terbium(III), dysprosium(III) and samarium (III).

The invention further provides use of the detectable molecule according to the invention in a biospecific binding assays.

DETAILED DESCRIPTION OF THE INVENTION

The aim of the present invention is to provide means to obtain improved lanthanide chelate labels to be used in specific bioaffinity based binding assays, such as immunoassays (both heterogeneous and homogenous assays), nucleic acid hybridization assays, receptor binding assays, immunocytochemical or immunohistochemical assays utilizing fluorometric or time-resolved fluorometric determination of the specific luminescence.

The chelates of this invention aim to combine several important features in a single label, such as 1. high absorptive at suitable wavelength, preferable over 300 nm,
2. several separate UV absorbing parts (chromophors) in the same ligand structure, preferable two chromophors,
3. effective energy transfer from the UV absorbing part (triplet sensitizer) to the lanthanide ion, 4. a strongly chelating part to create a) the thermodynamic stability required for storing the labelled reactants for extended periods of time, and b) high kinetic stability to allow the use of reactants in conditions where competing metal ions or chelating agents may be present,
5. a chelating part for as complete protection of the chelated ion as possible, preferable nine-dentate ligand,
6. a functional group allowing effective coupling of the chelate to be used as a binding reactant (e.g. antibody) without destroying its binding properties and decreasing the luminescence properties of the label,
7. functional groups to allow high water solubility and to prevent formation of aggregates during labelling of biomolecules and their unspecific binding of labelled biomolecules.

The present invention concerns detectable molecules comprising a biospecific binding reactant attached to a luminescent lanthanide chelate as defined above.

Methods applicable for attaching the biospecific binding reactant to the luminescent lanthanide are disclosed in prior art, e.g. in Bioconjugate Techniques, G. T. Hermanson, Academic Press (1996).

Preferably $R_{1A}$ and $R_{1B}$ are the same.

The term biospecific binding reactant as used herein refers to any substance or molecule capable of binding another molecule. The biospecific binding reactant is typically selected from a group consisting of an antibody, an antigen, a receptor ligand, a specific binding protein or peptide, a nucleic acid molecule, and a deoxyribonucleic acid (DNA) probe, a ribonucleic acid (RNA) probe, nucleic acid derivatives [such as peptide nucleic acid (PNA) and locked nucleic acid (LNA)] and chimeric molecules comprising nucleic acids (DNA and/or RNA) and/or nucleic acid derivatives, including but limited to chimeric probe molecules comprising DNA, RNA, PNA and/or LNA.

The term biospecific binding assay as used herein refers to methods and techniques that are used to determine the presence or the presence and quantity of an analyte molecule in a sample. Biospecific binding assays include but are not limited to immunoassays, nucleic acid hybridization assays, nucleic acid amplification assays, based on e.g. polymerase chain reaction (PCR), ligase chain reaction, nucleic acid sequence based amplification (NASBA) or rolling circle amplification reaction, receptor-binding assays and cellular binding assays. Biospecific binding assays can be homogeneous or heterogeneous. In homogeneous assays all assay components are present in one solution phase and it is not necessary to physically separate bound label molecules from unbound label molecules to detect biospecific binding events, whereas, in heterogeneous assays, biospecific binding events only become detectable after separation of bound label from unbound label.

The present invention also concerns the use of the detectable molecules of the invention in biospecific binding assays. In these assays the improvement in comparison to prior art comprises using the detectable molecule of the invention instead of detectable molecules of prior art.

The present invention further concerns a luminescent lanthanide chelate as defined above.

If the linker group $R_3$ of the invention is a activated derivative of an amino, aminooxy, carbonyl, aldehyde or mercapto group it can be selected from the group consisting of a isocyanato, isothiocyanato, diazonium, bromoacetamido, iodoacetamido, reactive esters, pyridyl-2-dithio and 6-substituted 4-chloro-1,3,5-triazin-2-ylamino.

The substituents in 6-substituted-1,3,5-triazine-2,4-diamine and 6-substituted 4-chloro-1,3,5-triazin-2-ylamino can be selected from the group consisting of hydrogen, halogen, alkoxy, aryloxy, amino, alkyl with 1 to 6 carbon atoms, substituted amino or thioethers, and preferable selected from the group consisting of chloro, fluoro, ethoxy, 2-methoxyethoxy, 2-cyanoethoxy, 2,2,2-trifluoroethoxy, thiophenoxy or ethoxycarbonylthiomethoxy. The substituted amino or thioether is preferably mono- or disubstituted each substitution being preferably independently selected from the group consisting of an alkyl or alkoxy with 1 to 6 carbon atoms, phenyl, carbonyl and carboxyl.

If the $R_3$ group is to be attached to a solid support it preferably has a reactive group, which is a polymerizing group.

If the chelating ligand is to be used in peptide or oligonucleotide synthesis as a means to prepare a label peptide or a labelled oligonucleotide as described in e.g. US 2005/0181393, the bridge between two chromophors, i.e. $R_3$-Ph-$CH_2$—$CH_2$—, it is preferable that the bridge comprises a functional group as described e.g. US 2005/0181393.

According to a preferred embodiment of the invention the lanthanide ion is either terbium(III). or dysprosium(III).

The following examples demonstrate the suitability of the labelling reagents for bioassays. Examples 8 discloses a quenching based homogeneous hybridization assay and example 9 a homogeneous detection of a PCR product.

It is noteworthy that a compound corresponding to chelate 7 of the examples with two 2,4,6-trimethoxyphenylpyridine moieties, i.e. {2,2',2'',2'''-{[2-(4-isothiocyanatophenyl)ethylimino]bis(methylene)bis[4-(2,4,6-trimethoxyphenyl)pyridine-6,2-diyl]bis(methylenenitrilo)}tetrakis(acetato)}terbium(III), has a very low aqueous solubility, and therefore, is unsuitable as a labelling reagent.

The structures and the synthetic route employed in the examples are shown in a reaction scheme 1. The scheme illustrates the synthesis of compound 7 exemplified by examples 1 to 7.

EXAMPLES

Example 1

Synthesis of 4-iodo-3-methoxyphenol (1)

3-Methoxyphenol (2.0 ml, 18.2 mmol) was dissolved in dry DMF (50 ml). Sodium iodide (3.3 g, 21.9 mmol) and chloramine-T (5.0 g, 21.9 mmol) was added to the mixture and the reaction was stirred at room temperature for one hour. The reaction mixture was diluted with water (150 ml), acidified with 5% hydrochloric acid solution and extracted with ethyl acetate (2×100 ml). The organic layer was washed with 5% sodium thiosulphate solution (200 ml) and dried over sodium sulphate. The product was purified by flash chromatography on silica gel twice (first with dichloromethane, then with 20% ethyl acetate in petroleum ether). The yield was 0.82 g (18%). $^1$H NMR (CDCl$_3$, 500 MHz): δ 7.52 (1H, d, J=8.5 Hz), 6.63 (1H, d, J=3.0 Hz), 6.37 (1H, dd, J=8.5 Hz, 3.0 Hz), 5.27 (1H, s), 3.81 (3H, s).

Example 2

Synthesis of tert-butyl(4-iodo-3-methoxyphenoxy)acetate (2)

Compound 1 (0.8 g, 3.19 mmol) was dissolved in dry DMF (30 ml). Dried potassium carbonate (1.32 g, 9.57 mmol) was added and the mixture was deaerated with argon. Tert-butyl bromoacetate (0.71 ml, 4.78 mmol) was added to the mixture and the reaction was stirred overnight at 70° C. The reaction mixture was cooled to room temperature and diluted with water (20 ml). The product was extracted with diethyl ether (3×50 ml) and dried over sodium sulphate. The product was purified by flash chromatography on silica gel using dichloromethane as an eluent. The yield was 1.1 g (96%). $^1$H NMR (CDCl$_3$, 500 MHz): δ 7.66 (1H, d, J=8.5 Hz), 6.39 (1H, dd, J=8.5 Hz, 2.5 Hz), 6.34 (1H, d, J=2.5), 4.57 (2H, s), 3.79 (3H, s), 1.51 (9H, s).

Example 3

Synthesis of tert-butyl[3-Methoxy-4-(4,4,5,5-tetramethyl-[1,3,2]dioxaborolan-2-yl)-phenoxy]acetate (3)

Compound 2 (1.05 g, 2.88 mmol) was dissolved in dry DMF (20 ml). Bis(pinacolato)diboron (0.88 g, 3.46 mmol) and potassium acetate (0.85 g, 8.64 mmol) were added and the reaction mixture was deaerated with argon. Palladium acetate (19.3 mg, 0.086 mmol) was added and the reaction was stirred for three hours at 85° C. The reaction mixture was cooled to room temperature and diluted with water (40 ml) and ethyl acetate (40 ml). Black particles were removed by filtration through a pad of Celite. The organic layer was separated, washed with water (30 ml) and dried over sodium sulphate. The product was purified by flash chromatography on silica gel using 3% methanol in dichloromethane as an eluent. The yield was 0.26 g (25%). $^1$H NMR (CDCl$_3$, 500 MHz): δ 7.79 (1H, d, J=8.5 Hz), 6.59 (1H, dd, J=8.5 Hz, 2.5 Hz), 6.31 (1H, d, J=2.5 Hz), 4.54 (2H, s), 3.83 (3H, s), 1.55 (9H, s), 1.28 (12H, s).

Example 4

Synthesis of tetra(tert-butyl)-2,2',2",2'"-{[2-(4-aminophenyl)ethylimino] bis-(methylene)bis{4-{2-methoxy-4-[(tert-butoxycarbonyl)-methoxy]phenyl}-pyridine-6,2-diyl}bis(methylenenitrilo)}tetra-kis(acetate) (4)

Compound 3 (0.11 g, 0.30 mmol) and tetra(tert-butyl)-2,2',2",2'"-{[2-(4-aminophenyl)ethylimino]-bis(methylene) bis(4-bromopyridine-6,2-diyl)bis(methylenenitrilo)}tetrakis(acetate) (0.10 mg, 0.10 mmol) were dissolved in dry DMF (5 ml) and the mixture was deaerated with argon. Caesium carbonate (0.11 g, 0.34 mmol) and tetrakis(triphenylphosphine)palladium (4.6 mg, 0.004 mmol) were added to the mixture and the reaction was stirred overnight at 80° C. The reaction mixture was cooled to room temperature and diluted with water (10 ml) and ethyl acetate (10 ml). Black particles were removed by filtration through a pad of Celite. The organic layer was separated, washed with brine (20 ml) and dried over sodium sulphate. The product was purified by flash chromatography on silica gel (first 5% methanol in dichloromethane and finally 10%). The yield was 90.0 mg (69%). $^1$H NMR (CDCl$_3$, 500 MHz): δ 7.63-7.72 (4H, m), 7.24 (2H, s), 6.90 (2H, d), 6.55 (2H, d), 6.50 (2H, d), 6.41 (2H, s), 4.42 (4H, s), 4.08 (4H, s), 3.96 (4H, s), 3.83 (6H, s), 3.53 (8H, s), 2.68-2.97 (4H, m), 1.45 (54H, m).

Example 5

Synthesis of 2,2',2",2'"-{[2-(4-aminophenyl)ethylimino]bis(methylene)bis{4-[2-methoxy-4-(carboxymethoxy)phenyl]pyridine-6,2-diyl}bis(methylenenitrilo)}-tetrakis(acetic acid) (5)

A solution of compound 4 (40.0 mg, 0.031 mmol) in trifluoroacetic acid (0.40 ml) was stirred at room temperature for 2 hours. After evaporation without heating, the mixture was triturated with diethyl ether (10 ml) and filtered. Filtration left a pure product. The yield was 53 mg. $^1$H NMR (d$_6$-DMSO, 400 MHz): δ 7.87 (2H, m), 7.75 (2H, s), 7.38 (2H, m), 7.17 (2H, m), 6.99 (2H, m), 6.68 (2H, d), 6.61 (2H, m), 4.74 (4H, s), 4.54 (4H, s), 4.09 (4H, m), 3.80 (6H, s), 3.56 (8H, s), 3.09 (4H, m).

Example 6

Synthesis of {2,2',2",2'"-{[2-(4-aminophenyl)ethylimino]bis(methylene)bis{4-[2-methoxy-4-(carboxymethoxy)phenyl]pyridine-6,2-diyl}bis(methylenenitrilo)}-tetrakis(acetato)}terbium(III) (6)

Compound 5 (49.2 mg, 0.038 mmol) was dissolved in water (1 ml) and the pH was adjusted to 6.5 with solid sodium hydrogen carbonate. Terbium(III) chloride hexahydrate (15.4 mg, 0.041 mmol) in water (0.2 ml) was added within 10 minutes and the pH maintained at 6.5 with solid sodium hydrogen carbonate. After stirring the reaction in room temperature for two hours, the pH was raised to 8.5 with 1 M sodium hydroxide and the precipitate was removed by centrifugation. The filtrate was treated with acetone and the product was collected by centrifugation and washed with acetone. The product was used in the next step without purification. The yield was 19.6 mg (47%). UV (50 mM carbonate buffer, pH 9.8): 308, 281. MALDI TOF-MS for $C_{48}H_{45}N_6O_{16}$Tb: calculated 1123.85, found 1122.85 (M−1)$^-$.

Example 7

Synthesis of {2,2',2",2'"-{[2-(4-isothiocyanatophenyl)ethylimino]bis(methylene) bis{4-[2-methoxy-4-(carboxymethoxy)phenyl]pyridine-6,2-diyl}bis(methylenenitrilo)}tetrakis(acetato)}terbium(III) (7)

Compound 6 (18.4 mg, 0.016 mmol) in water (0.5 ml) was added slowly to a mixture of thiophosgene (5.0 μl, 0.066 mmol), sodium hydrogen carbonate (6.9 mg, 0.082 mmol) and chloroform (0.5 ml). After stirring for one hour in room temperature, the water phase was washed with chloroform (3×1 ml). The pH of the aqueous solution was then adjusted to 7.0 with 1 M acetic acid and acetone was added. The product was collected by centrifugation and washed with acetone. The yield was 16.1 mg (84%). UV (50 mM carbonate buffer, pH 9.8): 310, 278. MALDI TOF-MS for $C_{49}H_{46}N_6O_{16}$STb: calculated 1165.91, found 1164.84 (M−1)$^-$.

Example 8

Quenching Efficiency

To characterize the suitability of the developed terbium chelate for quenching based homogeneous hybridization assays, a 5' amino-modified oligonucleotide probe having the sequence 5'-AAT TTA GAA GTC ATT AGC GAG CAG GCT ACC G-3' (SEQ ID NO 1) was labelled and purified in two different labelling and purification reactions with two different lanthanide chelates: with the chelate according to the present invention (compound 7) and with 2,2',2",2'"-{{6,6'-{4"-[2-(4-isothiocyanatophenyl)ethyl]-1H-pyrazole-1",3"-diyl}bis(pyridine)-2,2'-diyl}bis(methylenenitrilo)}tetrakis(acetato) terbium(III) (U.S. Pat. No. 5,859,215). The term "quenching based homogeneous hybridization assay", as used herein, refers to a method for nucleic acid detection as has been described for example by Kiviniemi et al. (Clin Biochem. 2003 November; 36(8):633-40. A homogeneous high-throughput genotyping method based on competitive hybridization. Kiviniemi M, Nurmi J, Turpeinen H, Lovgren T, Ilonen J.) The probe was labelled and purified with each chelate as described by Nurmi et al. (Anal Chem. 2002 Jul. 15; 74(14):3525-32. High-performance real-time quantitative RT-PCR using lanthanide probes and a dual-temperature hybridization assay. Nurmi J, Wikman T, Karp M, Lovgren T.). Hereafter, the two probes with the same base sequence but carrying different terbium chelates as labels are referred to as Probe 1 for the probe labelled with the chelate of the present invention (compound 7) and Probe 2 for the probe labelled with the chelate according to prior art.

In order to determine how efficiently the signals produced by Probe 1 and Probe 2 could be quenched with a complementary quencher probe, the following four kinds of reactions were prepared:

1. A 50 µl reaction containing 17 nM Probe 1 in 1×PCR Buffer II and 2.5 mM MgCl$_2$ (Applied Biosystems, Foster City, USA).
2. A 50 µl reaction containing 17 nM Probe 1 and 170 nM Quencher probe in 1×PCR Buffer II and 2.5 mM MgCl$_2$ (Applied Biosystems, Foster City, USA). The Quencher probe, which was complementary to Probe 1 and Probe 2, had the sequence 5'-TCG CTA ATG ACT TCT AAA TT-3'(SEQ ID No 2) and at its 3' end it carried the quencher label QSY7.
3. A 50 µl reaction containing 17 nM Probe 2 in 1×PCR Buffer II and 2.5 mM MgCl$_2$ (Applied Biosystems, Foster City, USA).
4. A 50 µl reaction containing 17 nM Probe 2 and 170 nM Quencher probe in 1×PCR Buffer II and 2.5 mM MgCl$_2$ (Applied Biosystems, Foster City, USA).

After the reactions were prepared, their terbium signals were measured using the default terbium measurement parameters of a Victor 2 Multilabel counter (PerkinElmer Life and Analytical Sciences Wallac, Finland). The maximum signal-to-noise ratios obtainable in a quenching based homogeneous hybridization assay with Probe 1 and Probe 2 were determined by dividing the signal obtained from reaction 1 by the signal of reaction 2 (for Probe 1) and by dividing the signal obtained from reaction 3 by the signal of reaction 4 (for Probe 2).

The results are shown in Table 1. As can be seen in the table, the signal intensity emitted by Probe 1 alone [597241 counts per second (cps)] is higher than the signal emitted by Probe 2 (134716 cps), indicating that the chelate according to the present invention (compound 7) is superior in comparison to the chelate according to the prior art because it is capable of providing a higher intensity of long lifetime fluorescence. Furthermore, the signal emitted by Probe 1 is quenched more efficiently by a complementary quencher probe than the signal emitted by Probe 2: the maximum signal-to-noise ratio obtainable using Probe 1 in a quenching based assay is approximately 65 while Probe 2 could theoretically only provide a signal-to-noise ratio of approximately 14. Therefore, it can be concluded that the chelate according to the present invention is highly suitable for use as a label in a quenching based hybridization assay.

TABLE 1

Quenching efficiencies obtainable with Probes 1 and 2. Probe 1 alone (reaction 1), labelled with the chelate of the present invention (compound 7), gives a higher signal than probe 2 alone (reaction 3), labelled with a chelate described in the prior art. The signal ratio between the free labelled probe 1 (reaction 1) and the quenched probe 1 (reaction 2) is higher than the ratio between the signals obtained from a free probe 2 (reaction 3) and a quenched probe 2 (reaction 4), which indicates that the chelate according to the present invention is more suitable for use as label in a homogeneous quenching-based hybridization assay than the chelate described in prior art.

| Reaction | Contents | Average terbium signal |
|---|---|---|
| 1 | Probe 1 alonen | 597 241 |
| 2 | Probe 1 and Quencher probe | 9 134 |
| 3 | Probe 2 alone | 134 716 |
| 4 | Probe 2 and Quencher probe | 9 640 |

Maximum theoretical signal-to-noise ratio for probe 1: 65
Maximum theoretical signal-to-noise ratio for probe 2: 14

Example 9

Suitability of the Chelate of the Present Invention for Homogeneous Detection of a PCR Product In order to characterize the suitability of the terbium chelate according to the present invention (compound 7) to homogeneous detection of a PCR product, Probe 1 (described above in example 8) was compared to Probe 2 (described above in example 8) in a polymerase chain reaction (PCR) assay that is specific to the bacterium *Listeria monocytogenes*. The signal generation principle of the PCR assay has been described by Nurmi et al. (Anal Chem. 2002 Jul. 15; 74(14):3525-32. High-performance real-time quantitative RT-PCR using lanthanide probes and a dual-temperature hybridization assay. Nurmi J, Wikman T, Karp M, Lovgren T.)

In order to obtain a comparison between the two different chelates, four different kinds of reactions were prepared as follows:
1. Negative control reactions with Probe 1 that did not contain any *Listeria monocytogenes* DNA
2. Positive control reactions with Probe 1 that contained 1000 copies of *Listeria monocytogenes* DNA to be amplified in the reaction
3. Negative control reactions with Probe 2 that did not contain any *Listeria monocytogenes* DNA
4. Positive control reactions with Probe 2 that contained 1000 copies of *Listeria monocytogenes* DNA to be amplified in the reaction The 30 µl PCR reactions consisted of 1× HotMaster Taq buffer (Eppendorf, Germany), 0.2 mM dNTPs, 0.3 µM forward primer (5'-GAT ACA GAA ACA TCG GTT GGC-3'; SEQ ID NO 3), 0.3 µM reverse primer (5'-GTG TAA TCT TGA TGC CAT CAG G-3'; SEQ ID NO 4), 28 nM Probe 1 or Probe 2, 280 nM Quencher probe (described above in example 1) and 1 unit of HotMaster Taq DNA polymerase (Eppendorf). Thermal cycling was performed on a 96 well plate in a PTC 200 DNA Engine (MJ Research, USA). The thermal cycling protocol consisted of an initial 2 minute denaturation step at 94° C. followed by 40 cycles of 30 seconds at 94° C. and 1 minute at 65° C., after which the reactions were cooled to 4° C. Terbium signals were recorded after thermal cycling using a Victor 2 Multilabel Counter using the default terbium measurement settings of the instrument. Signal-to-noise ratios (S/N) were calculated for the positive control reactions (reactions 2 and 4) by dividing the average terbium signal of reaction 2 or 4 by the average terbium signal of reaction 1 or 3, respectively.

The results of the experiment are shown in Table 2. As can be seen in the table, the negative control reactions containing Probe 1 gave an average signal of 80864 cps, while the respective positive control reactions containing Probe 1 produced a signal of 1 342 566 cps, resulting in a signal-to-noise ratio of 16.6. The higher signal in the positive control reactions is indicative of target DNA sequence amplification and clearly demonstrates that the chelate according to the present invention is highly suitable for use as a label in a homogeneous PCR assay. When Probe 2 was used instead of Probe 1, the signal intensities and signal-to-noise ratios were lower than with Probe 1: the average signal obtained from negative control reactions was 32 976 cps while positive control reactions gave an average signal of 248 393 cps, resulting in a signal-to-noise ratio of 7.5. The clear difference between the signal-to-noise ratios obtained with Probe 1 (S/N 16.6) and Probe 2 (S/N 7.5) indicates that the chelate of the present invention is superior compared to the chelate used in Probe 2 in that it is more suitable for use as a label in homogeneous PCR assays: it is capable of providing a higher signal intensity and a higher signal-to-noise ratio, which enables more sensitive detection of target nucleic acids and allows easier discrimination between positive and negative reactions.

TABLE 2

Terbium signals and signal-to-noise ratios obtained from PCR reactions 1, 2, 3 and 4.

| Reaction | Average terbium signal | S/N |
|---|---|---|
| 1 | 80 864 | — |
| 2 | 1 342 556 | 16.6 |
| 3 | 32 976 | — |
| 4 | 248 393 | 7.5 |

Scheme 1

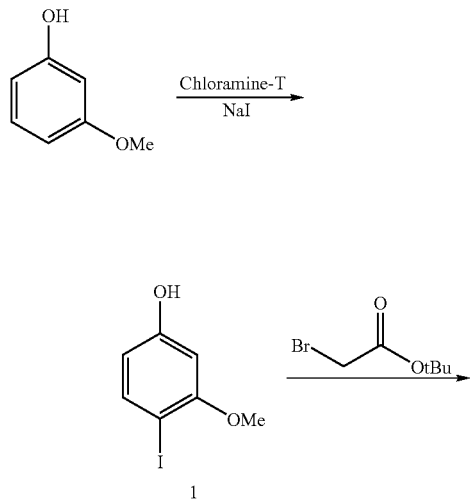

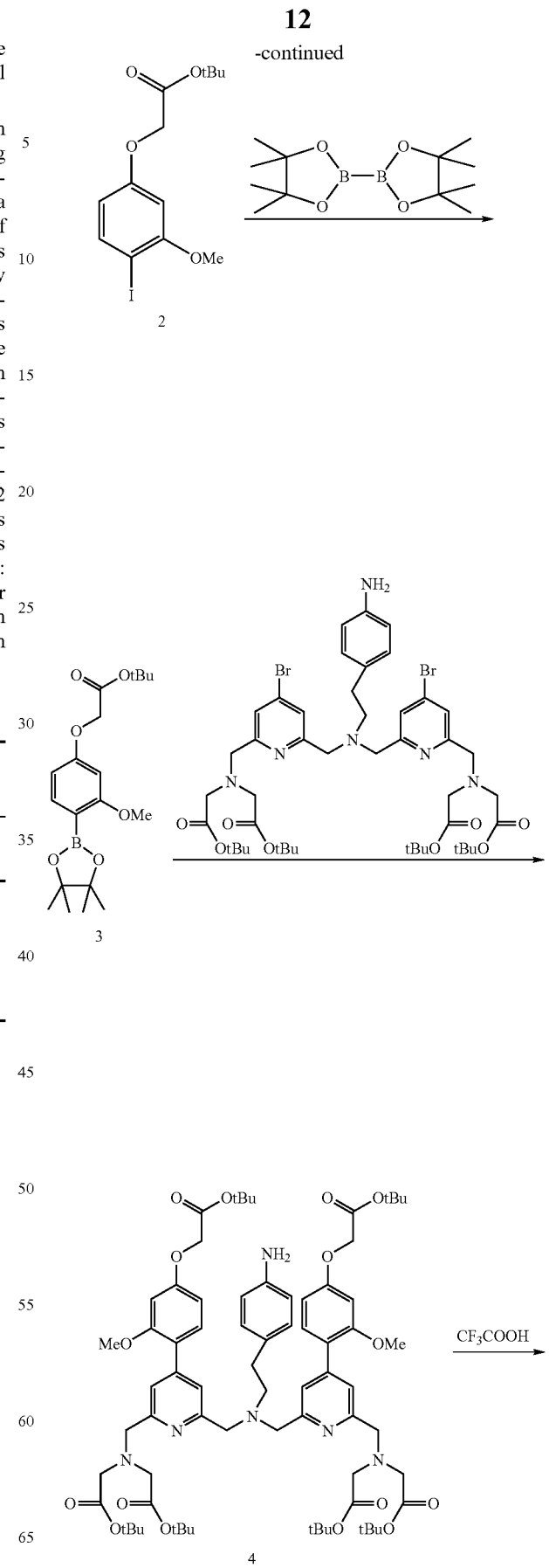

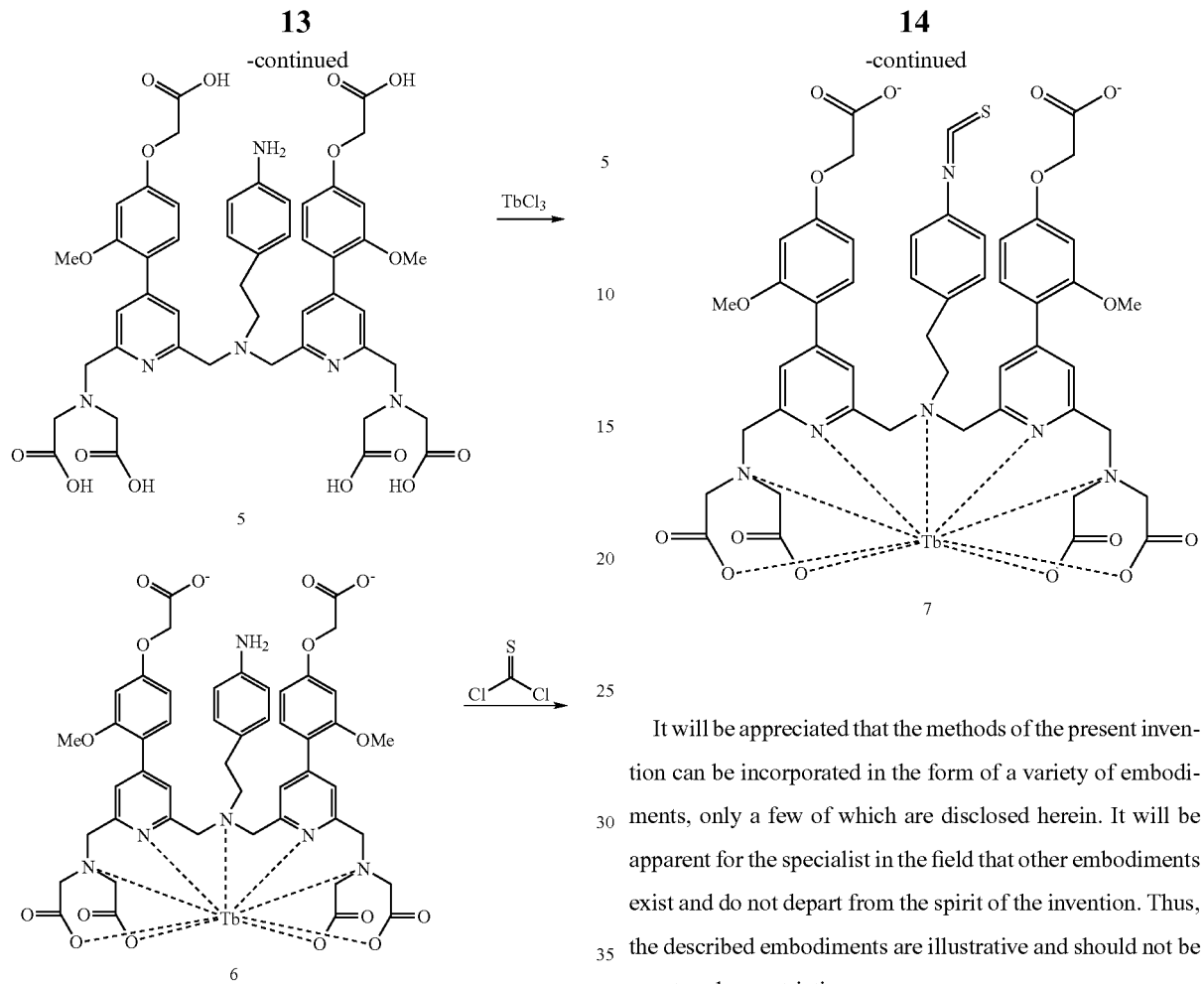

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A detectable molecule comprising a biospecific binding reactant attached to a luminescent lanthanide chelate comprising a lanthanide ion and a chelating ligand of the formula (I)

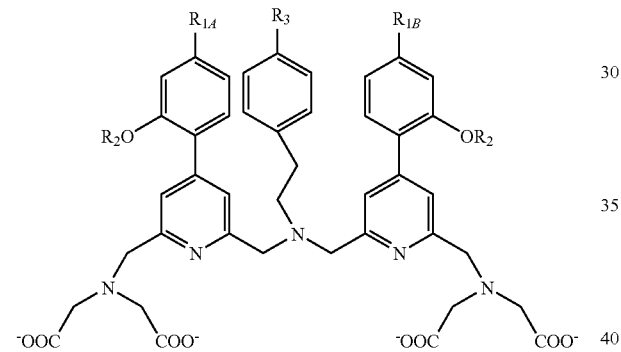

wherein, a) $R_{1A}$ and $R_{1B}$ are independently of each other selected from the group consisting of hydrogen, methyl, ethyl, —COOH, —COO—, —CH$_2$COOH, —CH$_2$COO—, hydroxyl and OR$_2$;

b) $R_2$ is selected from the group consisting of —CH$_3$, —C(CH$_3$)$_3$, —C(CR$_4$)$_3$, wherein $R_4$ is an alkyl with 1 to 6 carbon atoms, —CH$_2$COOH, —CH$_2$COO—,

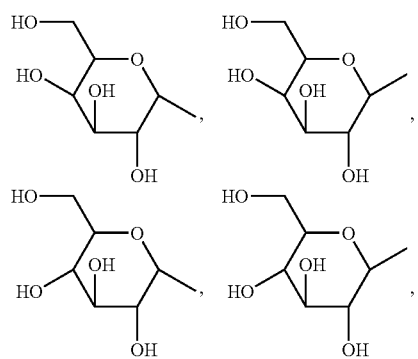

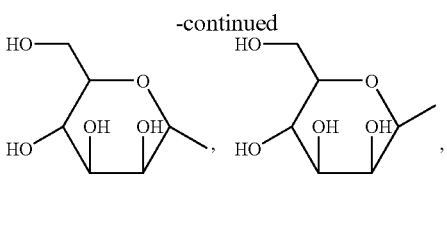

c) $R_3$ is a linker for coupling to said biospecific binding reactant selected from the group consisting of thiourea (—NH—CS—NH—), aminoacetamide (—NH—CO—CH$_2$—NH—), amide (—NH—CO— and —CO—NH—), aliphatic thioether (—S—), disulfide (—S—S—) and 6-substituted-1,3,5-triazine-2,4-diamine; and d) the lanthanide ion is selected from the group consisting of europium(III), terbium(III), dysprosium(III) and samarium(III).

2. The detectable molecule according to claim 1, wherein the biospecific binding reactant is selected from the group consisting of an antibody, antigen, a receptor ligand, a specific binding protein or peptide, a nucleic acid molecule, a DNA or RNA probe, nucleic acid derivatives and chimeric molecules comprising nucleic acids and/or nucleic acid derivatives.

3. The detectable molecule according to claim 1, wherein the lanthanide chelate attached to the biospecific binding reactant is {2,2',", 2'''-{[2-(4-iso-thiocyanatophenyl)-ethylimino]bis(methylene)bis{-4-[2-methoxy-4-(carboxymethoxy)phenyl]pyridine-6,2-diyl}bis(methylenenitrilo)}tetrakis(acetato)}terbium(III).

4. The detectable molecule according to claim 1, wherein the linker R3 is 6-substituted-1,3,5-triazine-2,4-diamine and the 6-substitution is selected from the group consisting of hydrogen, halogen, alkoxy, aryloxy, amino, alkyl with 1 to 6 carbon atoms, substituted amino or thioethers.

5. A luminescent lanthanide chelate comprising a lanthanide ion and a chelating ligand of formula (I)

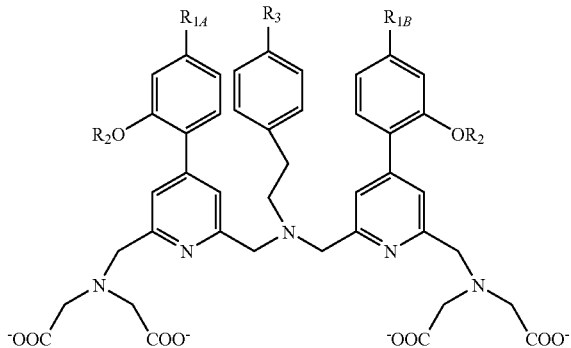

wherein,
a) $R_{1A}$ and $R_{1B}$ are independently of each other selected from the group consisting of hydrogen, methyl, ethyl, —COOH, —COO—, —CH$_2$COOH, —CH$_2$COO—, hydroxyl and OR$_2$;
b) $R_2$ is selected from the group consisting of —CH$_3$, —C(CH$_3$)$_3$, —C(CR$_4$)$_3$, wherein R$_4$ is an alkyl with 1 to 6 carbon atoms, —CH$_2$COOH, —CH$_2$COO—,

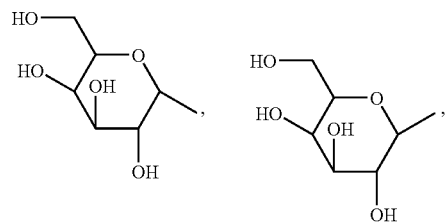

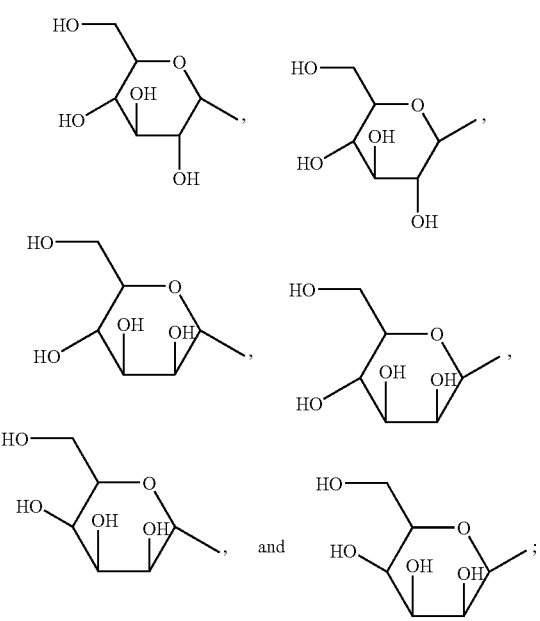

c) R$_3$ is a linker for coupling to a biospecific binding reactant selected from the group consisting of amino, aminooxy, carboxyl, aldehyde or mercapto groups and activated derivatives thereof; and
d) the lanthanide ion is selected from the group consisting of europium(III), terbium(III), dysprosium(III) and samarium(III).

6. A luminescent lanthanide chelate according to claim 5, wherein the linker R3 is a activated derivative selected from the group consisting of isocyanato, isothiocyanato, diazonium, bromoacetamido, iodoacetamido, reactive esters, pyridyl-2-dithio and 6-substituted 4-chloro-1,3,5-triazin-2-ylamino.

7. A luminescent lanthanide chelate according to claim 5, wherein the linker R3 is a 6-substituted 4-chloro-1,3,5-triazin-2-ylamino and the 6-substitution is selected from the group consisting of hydrogen, halogen, alkoxy, aryloxy, amino, alkyl with 1 to 6 carbon atoms, substituted amino or thioethers.

8. A biospecific binding assay method comprising:
labelling an analyte with the detectable molecule according to claim 1;
exciting said labelled analyte; and
detecting said excited labelled analyte.

9. A biospecific binding assay method comprising:
labelling an analyte with the detectable molecule according to claim 2;
exciting said labelled analyte; and
detecting said excited labelled analyte.

10. A biospecific binding assay method comprising:
labelling an analyte with the detectable molecule according to claim 3;
exciting said labelled analyte; and
detecting said excited labelled analyte.

11. A biospecific binding assay method comprising utilizing the detectable molecule according to claim 4, wherein the method comprises:
labelling an analyte with the detectable molecule according to claim 4;
exciting said labelled analyte; and
detecting said excited labelled analyte.

12. A detectable molecule according to claim 4, wherein the 6-substitution is selected from the group consisting of chloro, fluoro, ethoxy, 2-methoxyethoxy, 2-cyanoethoxy, 2,2,2-trifluoroethoxy, thiophenoxy and ethoxycarbonylthiomethoxy.

13. A luminescent lanthanide chelate according to claim 5 wherein the 6-substitution is selected from the group consisting of chloro, fluoro, ethoxy, 2-methoxyethoxy, 2-cyanoethoxy, 2,2,2-trifluoroethoxy, thiophenoxy and ethoxycarbonylthiomethoxy.

* * * * *

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial
<220> FEATURE:
<223> OTHER INFORMATION: Probe 1 and 2, example 8

<400> SEQUENCE: 1
aatttagaag tcattagcga gcaggctacc g                              31

<210> SEQ ID NO 2
<211> LENGTH: 20
<212> TYPE: DNA
<213> ORGANISM: Artificial
<220> FEATURE:
<223> OTHER INFORMATION: Quencher probe, example 8

<400> SEQUENCE: 2
tcgctaatga cttctaaatt                                            20

<210> SEQ ID NO 3
<211> LENGTH: 21
<212> TYPE: DNA
<213> ORGANISM: Artificial
<220> FEATURE:
```

```
<223> OTHER INFORMATION: Forward primer, example 9

<400> SEQUENCE: 3
gatacagaaa catcggttgg c                                        21

<210> SEQ ID NO 4
<211> LENGTH: 22
<212> TYPE: DNA
<213> ORGANISM: Artificial
<220> FEATURE:
<223> OTHER INFORMATION: Reverse primer, example 9

<400> SEQUENCE: 4
gtgtaatctt gatgccatca gg                                       22
```